United States Patent [19]
Antanavich et al.

[11] Patent Number: 5,814,022
[45] Date of Patent: Sep. 29, 1998

[54] METHOD AND APPARATUS FOR APPLYING TISSUE SEALANT

[75] Inventors: Richard D. Antanavich, Paso Robles; Randel Dorian, Orinda, both of Calif.

[73] Assignee: Plasmaseal LLC, San Francisco, Calif.

[21] Appl. No.: 595,936

[22] Filed: Feb. 6, 1996

[51] Int. Cl.⁶ .................................................. A61M 5/00
[52] U.S. Cl. ...................... 604/191; 604/181; 604/187; 604/208
[58] Field of Search ................ 604/82, 83, 181, 604/187, 191, 207, 208, 209, 210, 211, 227

[56] References Cited

U.S. PATENT DOCUMENTS

| | | | |
|---|---|---|---|
| 3,767,085 | 10/1973 | Cannon | 222/82 |
| 4,322,298 | 3/1982 | Persidsky | 210/787 |
| 4,424,132 | 1/1984 | Iriguchi | 210/800 |
| 4,610,666 | 9/1986 | Pizzino | 604/191 |
| 4,735,616 | 4/1988 | Eibl et al. | 604/191 |
| 4,979,942 | 12/1990 | Wolf et al. | 604/83 |
| 5,032,117 | 7/1991 | Motta | 604/191 |
| 5,074,844 | 12/1991 | Zdeb | 604/83 |
| 5,104,375 | 4/1992 | Wolf et al. | 604/56 |
| 5,116,315 | 5/1992 | Capozzi | 604/82 |
| 5,152,905 | 10/1992 | Pall et al. | 210/767 |
| 5,226,877 | 7/1993 | Epstein | 604/35 |
| 5,372,586 | 12/1994 | Haber et al. | 604/191 |
| 5,445,614 | 8/1995 | Haber et al. | 604/191 |
| 5,478,323 | 12/1995 | Holm | 604/191 |
| 5,505,704 | 4/1996 | Pawelka | 604/191 |
| 5,510,102 | 4/1996 | Cochrum | 424/78.08 |
| 5,520,657 | 5/1996 | Seller | 604/191 |
| 5,520,658 | 5/1996 | Holm | 604/191 |
| 5,542,934 | 8/1996 | Silver | 604/191 |

OTHER PUBLICATIONS

Vox Sanquinis, vol. 68: 82–89, Feb. 1995, Boomgaard et al., Pooled Platelet Concentration Prepared by the . . .

*Primary Examiner*—Michael Powell Buiz
*Assistant Examiner*—Daphna Shai
*Attorney, Agent, or Firm*—William B. Walker

[57] ABSTRACT

A device and method for applying a fibrinogen-based tissue sealant to seamlessly connect human or animal tissues or organ parts, to seal wounds, stop bleeding and the like by mixing fibrin or fibrinogen with blood clot-promoting coagulation factors are disclosed. The device includes two cylindrical compartments for separately containing the separate fluid components of the sealant preparation, which are simultaneously displaced from the respective compartments by means of plungers commonly depressable with the same effective strokes. The plungers may be depressed directly or by means of a common mechanism (e.g., rack and pinion) for accurately controlling the rate of dispensing fluid. The cylindrical compartments are of the same or different cross-sectional area and are arranged either concentrically or side-by-side. The device further includes a means for merging the two fluid components within an outer sleeve housing an inner needle. The sleeve and needle contain conduits for the flow of the two fluid sealant components as they are expressed from the respective compartments. Also disclosed are a convenient means of filling the two compartments, a means for mixing the fluid components, and for atomizing the effluent sealant fluid stream (i.e., spraying).

10 Claims, 6 Drawing Sheets

METHOD AND APPARATUS FOR APPLYING TISSUE SEALANT

BACKGROUND OF THE INVENTION

1. Field of the Invention

The present invention relates generally to the design of an improved delivery apparatus for applying two component fibrinogen/thrombin tissue sealants. More particularly, this invention is directed to the design of an apparatus that is easy to use and to fill, that allows accurate dispensing of small volumes and rapid dispensing of large volumes of tissue sealant, that allows minimal dilution of the fibrinogen component, and that ensures thorough mixing of the two sealant components, thus promoting rapid coagulation with a minimal amount of thrombin to produce a homogeneous tissue sealant.

2. Discussion of the Background

Clotting of blood in vivo takes place by conversion of the soluble plasma protein fibrinogen into fibrin, which spontaneously polymerizes into an insoluble gel matrix which may attach to adjacent tissue. The gel matrix stops bleeding and stabilizes structures. Thrombin catalyzed conversion of fibrinogen to fibrin can be reproduced in vitro and has great utility for adhering tissues and achieving hemostasis. Such fibrin sealants and fibrin glues are available commercially and are also made in blood processing laboratories. Preparation and use of fibrinogen-based sealants have been extensively reviewed[1].

Fibrin sealants, fibrin glues and adhesives based on combining fibrinogen-containing solutions with thrombin-containing solutions are used to reduce bleeding and restore hemostasis during surgical procedures. They have been known and in use for many years during which technology has evolved significantly. For example, fibrin clots can be made using different concentrations of fibrinogen in conjunction with the thrombin solution[2]. Subsequent developments in technology include cryoprecipitate fibrinogen[3]. Concentrated plasma can be used as the fibrinogen component in fibrin sealants[4].

Similarly, various types of applicators for fibrin glue are known[5]. An optimal design is not obvious because of the chemical and biological properties of the liquid resulting from combining fibrinogen and thrombin solutions. Because of the rapid polymerization upon intimate interaction of fibrinogen and thrombin, it is important to keep separate these two blood proteins until application to the site of use. In practice, the two components are typically dispensed simultaneously from separate syringes and brought together by means of an applicator manifold.

For example, one syringe-type apparatus for applying a tissue adhesive includes a plurality of standardized one-way syringe bodies of synthetic material[6]. Each syringe body accommodates a plunger and ends in a conus. The apparatus also includes a means for holding together the various syringe bodies, a guide rod, common actuating means and a head collecting the coni of said syringe bodies. This design, however, does not appear prevent clogging when flow of materials is interrupted during the course of its use in applying these materials to a surface. The connecting head brings the two materials together and the materials then travel together to a single mixing needle. Because of the rapid coagulation of the materials on mixing, this arrangement facilitates clogging of the apparatus (and in particular, the head or manifold), thus rendering the apparatus unusable.

In a later design, a medicinal gas is used to clear the mixing needle and address the clogging problem[7]. It is acknowledged that the tissue adhesive may set in the mixing needle in case of an interruption of the flow of the components during application or when using long and thin mixing needles. Consequently, the mixing needle must be exchanged immediately (e.g., upon interruption of use). However, from a practical perspective, the use of a medicinal gas is not suitable for most situations.

Similar arrangements/designs may be subject to the same deficiency, clogging. One design makes use of a ribbon-like separation means to confine clogging to a disposable tip[8]. Another design has the useful feature of specifying that the two syringes have different cross sections[9]. This arrangement includes a plurality of syringe bodies having equal effective strokes, each of the syringe bodies ending in joining pieces; a piston in each syringe body for commonly actuating them; and a connecting head attached to the joining pieces of the syringe bodies and provided with a separate conveying channel for each of the components to be applied. In this design, one of said syringe bodies has a cross-sectional area that is two to nine times larger than the cross-sectional area of the remaining syringe bodies. The larger syringe body contains an adhesive protein solution having a fibrinogen content of from 3 to 12%.

One reason for this arrangement/design is that the strength of the sealant is proportional to the fibrinogen concentration. Further, since cryoprecipitate fibrinogen is not very soluble a smaller volume of thrombin solution is useful in making a gel with greater adhesive and tensile strength.

An alternative embodiment that may help to minimize the clogging problem arranges for the two components to meet and mix within a disposable mixing tip[10]. This apparatus includes a plurality of distinct, elongate chambers containing fluids, each chamber including a piston for forcibly ejecting the fluid therefrom through a tapered nozzle; needle means having a corresponding plurality of interior conduits for dispensing fluid from said nozzles; lock means including a ridge projecting about an exterior surface of each tapered nozzle; and releasable retaining means comprising a separable needle and a releasable retaining means comprising a separable needle block having a fluid conduit with an interior groove for engaging a corresponding nozzle ridge and means for retaining associated needle means in sealing relationship with the chamber nozzles and the fluid conduits.

The apparatus, however, may be inappropriate for use in delicate microsurgical applications. Separation of the two components in separate channels in the mixing tip is effective but not optimal.

It is known that the tensile and adhesive strengths of fibrin sealants are best if the two solutions are mixed well, preferably rapidly to homogeneity[11]. One apparatus which addresses the clogging problem prevents commingling of the two sealant components until they reach the treatment site[12]. This apparatus, however, may not provide thorough and adequate mixing of the two solutions. The same limitation is found in an endoscope design[13].

Moreover, all of the heretofore referenced patents similarly fail to effectively address the issue of providing for thorough mixing of the sealant components during application, particularly if the apparatus is designed to overcome the clogging problem. This has two undesirable consequences: (1) the resultant gel is inhomogeneous and not as strong as that resulting from homogeneously mixed solutions and (2) more thrombin may be required to ensure rapid gelling. Risks associated with use of bovine thrombin make it undesirable to use excessive amounts. The U. S. Food and Drug Administration has expressed concern over coagulopathies associated with immunological reactions to commonly used bovine thrombin preparations[14]. The risk of zoonotic disease transmission has prompted the United Kingdom, Ireland and France to ban the use of bovine thrombin.

A method for conversion of autologous fibrinogen to non-cross-linked fibrin II or incomplete fibrinogen cleavage products (fibrin I or des BB fibrin, having one or the other of the two fibrinopeptides intact) using an insolubilized enzyme addresses a need for a thrombin-free fibrin glue[15]. The resulting unstabilized gel is dissolved by pH adjustment, separated from the insolublized enzyme, then mixed with buffer to restore conditions favorable to the repolymerization of the solubilized fibrin monomer solution, thus avoiding the addition of any soluble foreign animal protein (thrombin) to effect gelation of the sealant. A similar single protein solution method uses a mixture of thrombin and fibrinogen with an agent that inhibits the clotting activity of thrombin[16].

Limitations of these two methods include their multi-step nature and the consequent expense and time required to carry out the processes. Additionally, the molecular structure and physical and adhesive properties of the resultant gels are not likely to be equivalent to those of naturally formed clots[7].

Yet another limitation of previous applicator designs is that depressing syringe plungers may render accurate dispensing of small volumes of sealant (e. g., single drops) difficult. Proposed solutions to this difficulty include a dispenser with a push button actuator[18] and a device using a lever and ratchet and pawl mechanism[19] to dispense sealant components by pressure so that small volumes can be dispensed during delicate operations such as otological surgical procedures. Both of these devices are limited by the inability to rapidly dispense larger volumes of sealant when required, thus falling short of practical volume flexibility needs.

The use of unequal amounts of solutions within the syringe bodies dispensed simultaneously advantageously allows for minimizing dilution of the fibrinogen containing solution by the thrombin solution. However, filling the separate compartments with the respective sealant components and assembling the mechanical components comprising these devices can be complicated and time consuming.

One applicator, designed to produce a mist of mixed components[20], is similarly complicated to assemble and use. If care is not taken in assembly of the device, misalignment of the two syringes with respect to the applicator device and incomplete sealing of the syringe Luer ports into the docking ports of the applicator manifolds may occur. In addition, mixing takes place in a spray head which may clog after use.

Alternatively, the two components of a fibrinogen-based tissue sealant may be applied as separate aerosols and mixed in the field[21,22]. These devices may not allow for adequate mixing of the two sealant components, Consequently, greater amounts of thrombin and inferior gels may be produced, a problem inherent in field mixing.

REFERENCES

The following references are incorporated herein by reference, in their entireties or to any extent desired and/or necessary.

1. Matras, H. (1985). "Fibrin seal: the state of the art." *J Oral Maxillofac Surg* 43(8): 605–11.

Sierra, D. H. (1993). "Fibrin sealant adhesive systems: a review of their chemistry, material properties and clinical applications." *J Biomater Appl* 7(4): 309–52.

Thompson, D. F., N. A. Letassy, et al. (1988). "Fibrin glue: a review of its preparation, efficacy, and adverse effects as a topical hemostat." *Drug Intell Clin Pharm* 22(12): 946–52.

2. Ferry, J. D. and P. R. Morrison (1950). "Fibrin clots and methods for preparing the same." U.S. Pat. No. 2,553,004.

3. Alterbaum, R. (1987). "Method and apparatus for use in preparation of fibrinogen from a patient's blood." U.S. Pat. No. 4,714,457.

Lontz, J. F. (1995). "Phase Transfer Process For Producing Native Plasma Protein Concentrates." U.S. Pat. No. 5,420,250.

Matras, H., H. P. Dinges, et al. (1972). "Zur nahtlosen interfaszikularen Nerventransplantation im Tierexperiment." *Wein Med Woschtr* 122(37): 517–523.

Rose, E. and A. Dresdale (1986). "Fibrin adhesive prepared as a concentrate from single donor fresh frozen plasma." U.S. Pat. No. 4,627,879.

4. Antanavich, R. and R. Dorian (1995). "Plasma concentrate and tissue sealant compositions . . . ." U.S. patent application Ser. No. 08/351,010.

5. See Section 4, pages 320–321, in Sierra, D. H. (1993). "Fibrin sealant adhesive systems: a review of their chemistry, material properties and clinical applications." *J Biomater Appl* 7(4): 309–52.

6. Redl, H. and G. Kriwetz (1982). "Apparatus for applying a tissue adhesive on the basis of human or animal proteins." U.S. Pat. No. 4,359,049.

7. Redl, H. and G. Habison (1986). "Apparatus for Applying a tissue adhesive." U.S. Pat. No. 4,631,055.

8. Keller, W. A. and S. A. Chen (1988). "Dispensing and mixing apparatus." U.S. Pat. No. 4,767,026.

9. Eibl, J., G. Hobbesian, et al. (1988). "Arrangement for applying a tissue adhesive." U.S. Pat. No. 4,735,616.

10. Speer, S. J. (1977). "Packaging and dispensing kit." U.S. Pat. No. 4,040,420.

11. Thompson, D. F., N. A. Letassy, et al. (1988). "Fibrin glue: a review of its preparation, efficacy, and adverse effects as a topical hemostat." *Drug Intell Clin Pharm* 22(12): 946–52. See paragraph pp. 948–9.

Redl, H., G. Schlag, et al. (1982). "Methods of Fibrin Seal Application." *Thorac. cardiovasc. Surgeon* 30: 223–227.

Redl, H. and G. Schlag (1986). Fibrin Sealant and Its Modes of Application. *Fibrin Sealant in Operative Medicine*. G. Schlad and H. Redl. Heidelberg, Springer-Verlag: 13–26.

Shimada, J., K. Mikami, et al. (1995). "Closure of leaks by fibrin gluing. Effects of various application techniques and temperatures." *J Cardiovasc Surg (Torino)* 36(2): 181–4.

12. Miller, C. H., J. H. Altshuler, et al. (1989). "Fibrin glue delivery system." U.S. Pat. No. 4,874,368.

13. Maslanka, H. (1990). "Injection equipment with a twin tubular needle for an endoscope." U.S. Pat. No. 4,932,942.

14. Alving, B. M., M. J. Weinstein, et al. (1995). "Fibrin sealant: summary of a conference on characteristics and clinical uses." *Transfusion* 35(9): 783–90.

15. Edwardson, P. A. D., J. E. Fairbrother, et al. (1993). "Fibrin sealant compositions and method for utilizing same." EP (Application) Patent 592,242.

16. Morse, B. S., R. T. McNally, et al. (1994). "Fibrin sealant delivery kit." U.S. Pat. No. 5,318,524.

17. Sporn, L. A., L. A. Bunce, et al. (1995). "Cell proliferation on fibrin: modulation by fibrinopeptide cleavage." *Blood* 86(5): 1802–10.

18. Tang, R. A. (1986). A New Application Method for Fibrin Sealant: The Glue Gun. *Fibrin Sealant in Opera-* tive Medicine. G. Schlad and H. Redl. Heidelberg, Springer-Verlag.
19. Epstein, G. H. (1993). "Method and apparatus for preparing fibrinogen adhesive from whole blood." U.S. Pat. No. 5,226,877.
20. Capozzi, E., and H. S. Cooksten (1992). "Biological syringe system." U.S. Pat. No. 5,116,315.
Capozzi, E., and H. S. Cooksten (1990). "Biological syringe system." U.S. Pat. No. 4,978,336.
21. Avoy, D. R. (1990). "Fibrinogen dispensing kit." U.S. Pat. No. 4,902,281.
22. Lonneman, A. and C. H. Miller (1994). "Sprayer assembly for physiologic glue." U.S. Pat. No. 5,368,563.

OBJECTS OF THE INVENTION

The present invention disclosed herein addresses and solves the limitation of the prior devices. The present applicator is easy to assemble, can accurately dispense small volumes or rapidly dispense large volumes of sealant, minimizes dilution of the fibrinogen component, adequately mixes the two components, does not clog event when set aside for several minutes, and is relatively easy to fill, assemble, use and manufacture.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 3A, 3B and 3C show cross sections of three arrangements for the separate compartments for containing and dispensing the separate fibrinogen and gel-forming agent solutions: FIG. 3C shows and embodiment comprising coaxially arranged cylinders 10 and 11. The fibrinogen solution is put in the compartment with the larger cross section 12 and the thrombin and/or calcium solution is put in the compartment with the smaller cross section 13.

FIG. 4 is a cross-sectional view of an embodiment of the manifold 4 and applicator static mixer tip 5 of the syringe of FIG. 1. Swivel Luer locks 21 provide a means for attaching the syringes. Thrombin is dispensed through the inner needle 22 and fibrinogen through the void 23 between inner needle 22 and outer sleeve 25. Inserted static mixer device 26 fits snugly within the outer sleeve 25. Notched rings 28 on the rod mixer device ensure mixing of the two sealant components by creating turbulent flow. The distal tip 24 of the inner needle is located within the outer sleeve near the mixing device insert 26.

FIG. 5 shows a cross-sectional view of coaxially arranged cylindrical compartments as shown in FIG. 3C. The inner syringe 32 containing thrombin solution is coaxial with the large syringe 31 containing fibrinogen solution. The inner syringe plunger 34 operates normally, traveling through a hole or slot in the plunger for the outer compartment 35. The cylinders are maintained coaxial with a cylindrical washer 38 made of rubber of other suitable material. The needle 37 leading from the inner compartment 40 conducts the thrombin into the replaceable mixing tip 39.

FIG. 6 is a detailed cross-sectional view of the lower part of the coaxial syringe shown in FIG. 5. The mixing tip is removed. The needle 37 leading from the inner compartment 40 exits through the center of a male Luer lock 42. The fibrinogen solution in the outer compartment is conducted through a channel 41 in the washer 38 and exits from the male Luer lock around the inner chamber needle 37.

FIGS. 8, 9, 10 and 11 each show cross-sectional views of various embodiments of the manifolds and mixing tips of the present apparatus for applying tissue sealant. In all cases, the coaxial syringe shown in FIG. 5 is used. A Luer lock 42 is used to attach each of the four applicator tips to the double syringe.

FIG. 10 shows a spray tip 71. The two components mix in the tip 71 and the mixture is nebulized by a small orifice 72.

DETAILED DESCRIPTION OF THE PREFERRED EMBODIMENTS

The present invention concerns, in part, a dispenser comprising:
  a plurality of separate parallel cylindrical compartments of the same or different cross sectional area, arranged concentrically or side-by-side, each of said cylindrical compartments having an outlet port at one end,
  a number of plungers equal to said plurality of cylindrical compartments, and
  a manifold having separate means for transporting fluid through the manifold from the outlet port of each cylindrical compartment to a common location on the surface of the manifold opposite said outlet ports.

In further embodiments, the dispenser may further comprise a means for separately or commonly actuating said plungers in mechanical connection to said plungers, preferably both a means for commonly actuating said plungers and a means for separately actuating said plungers. The means for commonly actuating said plungers may comprise a rack and pinion mechanism. Alternatively, the means for commonly actuating said plungers comprises a bar, rod or other means for mechanically connecting said pinion to the cap of each plunger.

The cylindrical compartments of the dispenser may be coaxial, and said means for commonly actuating said plungers and said means for separately actuating said plungers may comprise a coaxial inner plunger having a cap and a coaxial outer plunger having a coaxial cylindrical void into which said inner plunger is located, the diameter of said cap being greater than the diameter of said cylindrical void. In other words, the cylindrical compartments may comprise inner and outer concentric compartments, the inner concentric cylindrical compartment being fitted with an inner plunger, and the outer concentric compartment being fitted with a cylindrical plunger having a coaxial cylindrical void within which said inner plunger is located.

In one embodiment, the present dispenser comprises two coaxial cylinders of different sizes. When the plurality of cylinders is 2, said cylinders may have equal heights, and the volume ratio of said cylinders may be 9 or more, preferably 10 or greater. In the present application, "coaxial cylinders" refers to cylinders which share a common axis, or parallel cylinders of different diameters in which the void of the smaller cylinder is contained within the larger cylinder.

The present dispenser may further comprise a manifold comprising separate inner and outer means for conveying the contents of said cylinders to a common outlet, wherein the inner means extends further than the outer means. The present dispenser may also further comprise a disposable tip which promotes mixing of said contents of the cylinders. In addition, the present dispenser may further comprising a means for atomizing effluent fluid in fluid connection to one end of said cylindrical fluid conduit.

Fibrinogen and thrombin solutions are contained separately within compartments in an apparatus comprising: (1) syringes held together side-by-side in a bracket, the plungers of said syringes commonly actuable or depressible by an activating means or (2) integral side-by-side cylinders fitted with coupled plungers for simultaneously expressing or dispensing the contents of said cylinders or, preferably, (3) coaxially arranged cylinders fitted with commonly (or separably) depressible or actuable plungers, the outermost of which is shaped to seal against both the inner wall of the outer cylinder and the outer wall of the inner cylinder.

Other factors being constant, tensile and adhesive strengths of tissue sealant are generally proportional to the concentration of fibrinogen after combination with thrombin. To minimize dilution of fibrinogen by the thrombin solution, the cross-sectional areas of the two compartments are preferably different so that a common stroke will displace a small amount of thrombin solution relative to fibrinogen solution. Any ratio of cross-sectional areas is workable. A ratio of cross-sectional areas of greater than 1:5 is preferable and a ratio of 1:10 up to 1:40 is most preferable.

The volume of the compartments may vary depending on the intended use. Tissue sealants are typically dispensed from fibrinogen preparations of volume ranging from 0.5 cc to 5 cc. As described above, the corresponding thrombin compartment typically would have a volume of one tenth to one fortieth the volume of the fibrinogen compartment.

In the embodiments of the present apparatus comprising side-by-side syringes or cylinders, to facilitate assembly, convenient fittings such as swivel Luer lock fittings or the like are provided for coupling to a manifold so that coupling can be effected without the necessity of rotating the syringes or cylinders relative to the assembly fixture and manifold. Alternatively, the two syringes or cylinders terminate in needles which may serve the dual functions of (1) facilitating filling with appropriate components of the fibrin sealant and (2) connecting to a manifold fitted with septa to mate with the needles, allowing fluid communication between the respective compartments and appropriate channels within the manifold.

A further aspect of the present invention concerns a manifold for combining the contents of a multicomponent dispenser, comprising a first inlet port, an inner fluid transport means in fluid connection with said first inlet port, said inner fluid transport means having a first outlet port located at the end opposite said first inlet port, a second inlet port distinct from the first inlet port, and an outer fluid transport means in fluid communication with said second inlet port, said outer fluid transport means having a second fluid outlet port located at the end opposite said second inlet port, wherein said second fluid outlet port is in the same location as said first outlet port and at least part of said inner fluid transport means is located within said outer fluid transport means.

Figure 4:
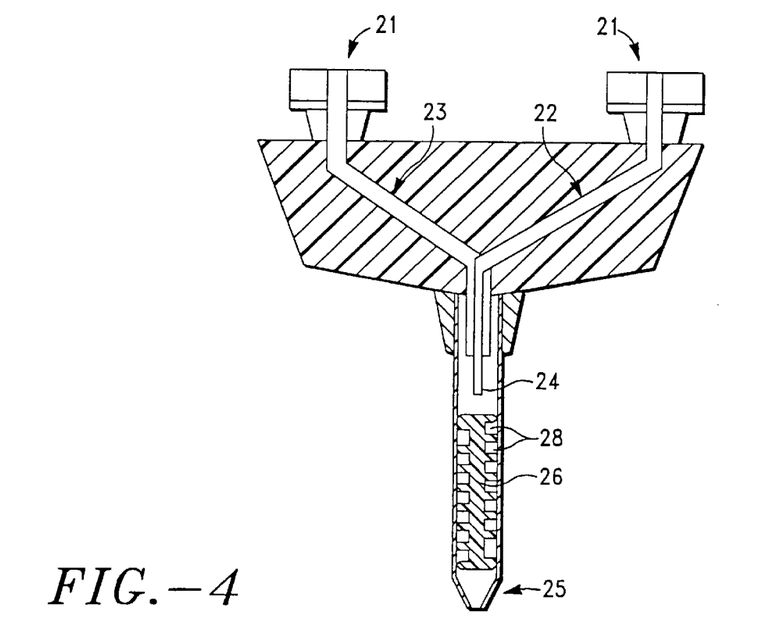

In more specific embodiments of the manifold, the inner fluid transport means and said first inlet port comprise a hypodermic needle, and said second inlet port and said outer fluid transport means comprises a channel in a solid material through which said hypodermic needle is located or is able to penetrate (see FIG. 4).

In order to minimize the problem of plugging due to coagulation of sealant within the manifold, the manifold is configured in such a way as to prevent commingling of the two sealant components until the expression of one component, through a needle or the like which separately conducts said component, into a flow of the second component within a sleeve, e.g. a larger bore hypodermic needle or the like, which surrounds said first hypodermic needle, the outer sleeve terminating at a point distal to the point at which commingling of the two fluids first occurs.

The needle conducting the lower-volume (e.g., thrombin) solution may be a standard 22 gauge needle, and the larger bore needle conducting the higher-volume (e.g., fibrinogen) solution may be a standard 18 gauge needle. The larger needle may be of any size from 3 to 25 gauge, and from 0.5 cm to 6 cm in length, preferably 1 to 3 cm. The smaller needle must fit within the larger and not obstruct flow.

In a further embodiment of the present apparatus comprising coaxially arranged cylinders, the contents of the inner compartment are in fluid communication with a hypodermic needle or the like which extends beyond the distal terminus of a coaxial effluent port of the outer compartment and which is of an outer diameter less than the inner diameter of said effluent port. The contents of said outer compartment are isolated from those of the inner compartment, but are in fluid communication with the effluent port of the outer compartment. By means of a Luer fitting or the like, an outer sleeve comprising a hypodermic needle or the like, of greater internal diameter than the outer diameter of the inner hypodermic needle described above, is affixed to the effluent port of the outer compartment. The outer sleeve extends beyond the distal terminus of the inner hypodermic needle. The volume of the compartments may vary depending on the intended use. Tissue sealants are typically dispensed from fibrinogen preparations of volume ranging from 0.5 cc to 5 cc. As described above, the corresponding thrombin compartment typically would have a volume of one tenth to one fortieth.

By commonly depressing the respective plungers of the inner and outer compartments, the contents of the separate compartments are expressed, dispensed or exhausted separately but simultaneously through the inner hypodermic needle and the outer sleeve. As they are expressed, the two separate fluid components merge at the distal terminus of the inner hypodermic needle within the outer sleeve. The merged fluids commingle and become mixed as they flow within the outer sleeve towards the distal terminus, becoming more thoroughly mixed by the time they are applied to the site of use. If flow is interrupted during sealant dispensing, a gel may form in the outer sleeve at a location between the distal terminus of the inner hypodermic needle to the distal terminus of the outer sleeve. The gel typically forms a short cylinder in the void within the outer sleeve and does not substantially adhere to the material of the outer sleeve or inner needle. Rather, the short gel cylinder extends from the distal terminus of the inner needle toward the distal terminus of the outer sleeve. Because of its shape, small size and lack of adherence to the surrounding outer sleeve, the gel which may form does not effectively plug the device and can be dispensed or expressed by resuming application of sealant without exerting perceptibly greater force to depress the commonly actuated plungers.

Mixing of the two fluid components as they are extruded is adequate for most applications, yielding strong gels which rapidly polymerize at low thrombin concentrations. optionally, if perfectly homogeneous mixing of the two fluid components is desirable, the outer sleeve may incorporate a static mixer comprising, for example, of parallel arcs centered on the axis of a shaft snugly fitted to the inner wall of the outer sleeve from a point just distal to the distal terminus of the inner hypodermic needle and extending to a point proximal to the distal terminus of the outer sleeve. Thus, the present invention also concerns a static mixing means, comprising:

a cylindrical fluid conduit, a coaxial shaft having parallel arcs thereon, fitted within said cylindrical fluid conduit, wherein said parallel arcs promote mixing of said fluid.

Adjacent arcs may be rotated about the axis of the cylinder to force a more tortuous and turbulent flow of the commingled fluids. Preferably, the arcs are positioned along the mixing tip so that the gaps of the rings are located opposite the gaps of the adjacent rings. Most preferably, the gaps on adjacent rings are on opposite sides. The static mixing insert may be of any length from 0.1 cm to 5 cm, preferably 0.25 to 1 cm. The number of arcs may range from two to fifty, preferably five to fifteen. Thus, each arc of the present mixing means may comprise a ring having a void of from 5° to 90°, the void of one ring being located opposite the void on adjacent ring(s).

On interruption of flow, coagulation of the sealant about the static mixer will occlude the flow path. Removing and replacing the outer sleeve and static mixer may be necessary in this embodiment. However, the combination of the outer sleeve and static mixer is inexpensive, and the method of removing and replacing this combination is a very simple operation which sacrifices a minute included volume of sealant and is completely effective in restoring functionality of the applicator device.

Prior to dispensing sealant as variously described above, the separate fibrinogen solution and thrombin or other clot-promoting solutions must be charged into the respective applicator compartments. For this purpose, a connecting tee can be used to direct the flow of the two solutions separately into the appropriate compartments.

Thus, a further aspect of the present invention concerns a device for filling a two-compartment dispenser, comprising a first means for fluidly connecting said device with an outlet port of a first container for fluid, a first means for transporting fluid from said first means for fluidly connecting said device to a first compartment of said dispenser, a second means for fluidly connecting said device to a second container for fluid, a second means for transporting fluid through said device from said second means for fluidly connecting said device to an outlet port for the other of said two compartments of said dispenser.

A more specific embodiment of the device for filling the present dispenser may comprise a cylindrical shaft having a Luer fitting at one end and a pierceable septum at the other end, and a Luer fitting attached to the outer wall of said cylindrical shaft.

Figure 7:
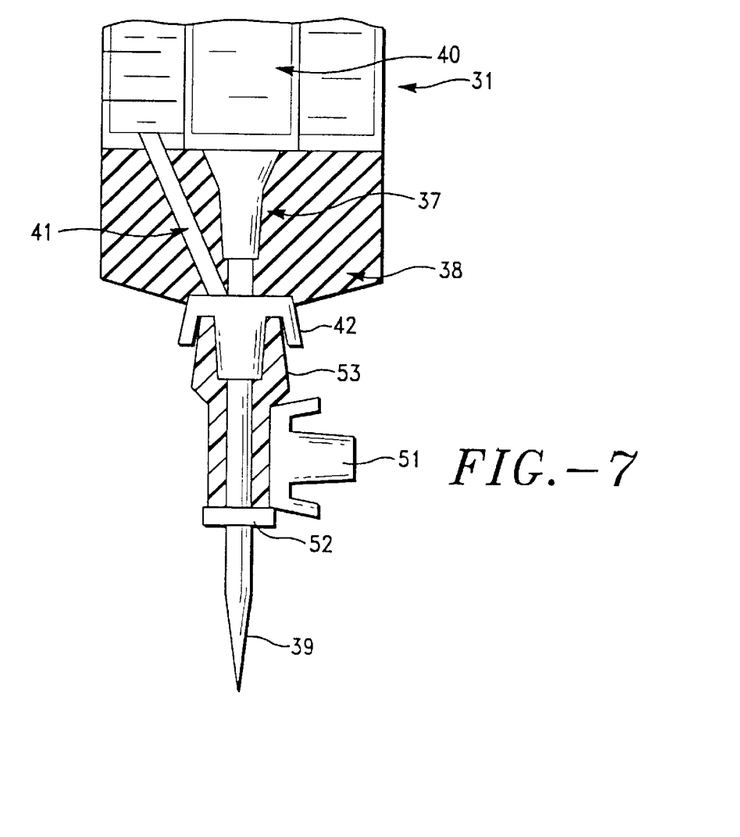
FIG. 7 is a cross-sectional view of an embodiment of a filling device (a "connecting tee") used to fill the two compartments of the coaxial syringe shown in FIG. 5. A female Luer lock 53 is joined with the male on the syringe 42. The needle 37 from the inner chamber 40 pierces a rubber septum 52. The inner needle tip 39 may then be used to fill the inner compartment (e.g. by piercing a septum on a container containing the gel-forming agent solution). The outer compartment may then be filled with fibrinogen solution by fluidly connecting a chamber containing fibrinogen solution to a male Luer lock 51.

As shown in FIG. 7, the tee comprises a female Luer coupling 53 or equivalent means for docking with the effluent port 42 of the outer compartment. The inner hypodermic needle 37 is directed through this coupling and pierces a septum 52 which seals the opposing end of the tee so that said hypodermic needle passes in a straight path through the tee and isolates its contents from the void within the tee and is free beyond the tee to collect the appropriate solution. The tee must be short enough that the needle pierces the septum but should not have excessive volume. The length thus may be as little as 0.5 cm and may be as long as slightly shorter than the inner needle. Preferably, the tee is 1.5 to 3 cm in length.

The inner plunger is separably actuable from the outer plunger and is pulled back separately from the outer plunger to withdraw appropriate solution from a source into the inner compartment. The orthogonal arm of the tee can be fitted with a hypodermic needle or tubing or the like. By separately pulling back the outer plunger, the second sealant component is withdrawn from a source through said hypodermic needle or tubing or the like and into the outer compartment. Alternatively, both solutions can be separately and simultaneously introduced into the appropriate compartments by pulling back simultaneously on both plungers while the inner hypodermic needle and appropriate means for the orthogonal arm of the tee to communicate fluidly with an appropriate fluid component source are simultaneously in separate fluid communication with the respective sealant component sources. The plungers are so arranged that each may be separately pulled back or both together.

The inner and outer plungers are separably actuable by virtue of an arrangement whereby the inner plunger moves freely and independently within a hollow outer plunger (i.e., the outer plunger contains a cylindrical void within which the inner plunger is located). The top of the outer plunger may comprise a button with a center opening of sufficient diameter to allow the inner plunger to move freely. A button on the top of the inner plunger, however, which is larger than the opening in the top of the outer plunger button engages the two plungers to move in concert when the upper plunger is depressed and encounters the outer plunger button. In other words, the hole in the center of the outer plunger has a diameter smaller than the diameter of the inner plunger button (e.g., insufficient to allow the inner plunger button to travel further without simultaneously effecting an equal stroke of the outer plunger). The bases of the inner and outer cylinders are tapered in such a way as to conduct air entrapped within the two compartments to a high point communicating with the respective effluent channels when the apparatus is inverted, thus permitting entrapped air to be expelled after filling and before application of sealant to the site of use.

Figures 1, 2:
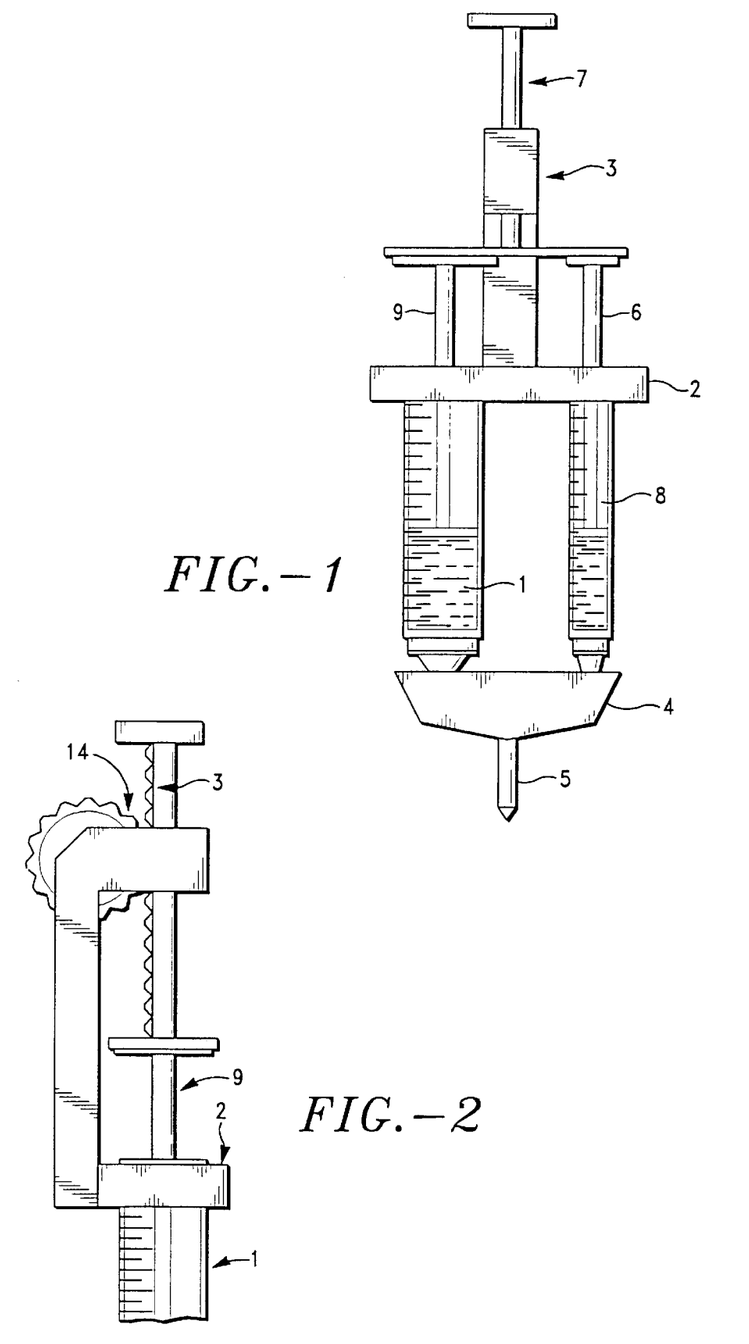
FIG. 1 shows an embodiment of the present invention employing two syringes 1 and 8 affixed in a bracket 2 with rack and pinion drive 3, manifold 4 and optional replaceable applicator static mixing tip 5. Syringes 1 and 8 are affixed to bracket 2. Syringe plungers 6 and 9 are depressed by movement of the rack 7.
FIG. 2 shows a side view of and embodiment of the bracket 2 and rack and pinion drive 3. Syringes 1 and 8 are affixed to bracket 2. Rack 3 can be depressed directly to rapidly dispense larger volumes of sealant, or the thumb wheel pinion 14 can be turned to displace small volumes accurately. Syringe plungers are depressed by movement of the rack.
Figure 3A:
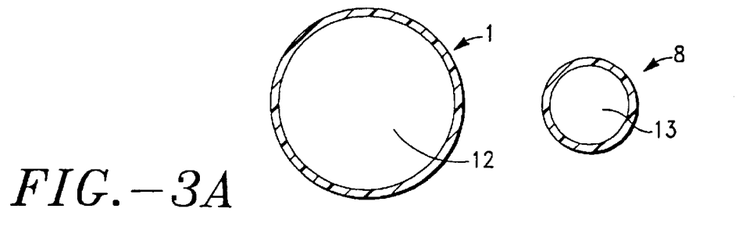
FIG. 3A shows syringes 1 and 8 held together side-by-side in a bracket as shown in FIGS. 1 and 2.
Figure 3B:
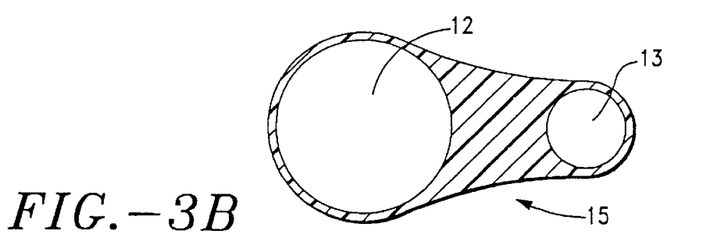
FIG. 3B shows integral side-by-side cylinders 15, made from a single mold.
Figure 3C:
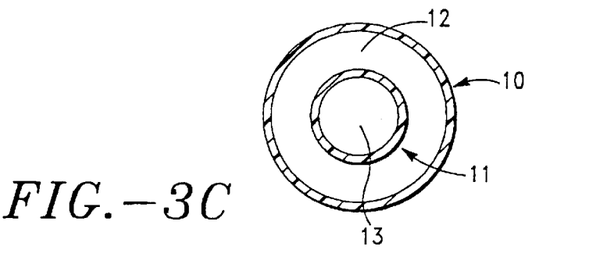

To permit accurately controlled dispensing of small volumes of sealant (e.g., single drops), depression of the commonly actuable plungers of any of the above described embodiments may be effected by a means for depressing the plungers (e.g., a rack and pinion mechanism driven, for example, by a thumb wheel pinion as shown in FIG. 2). When rapid dispensing of sealant is desired, said rack can be depressed directly. The rack and pinion may be used with any of the three cylinder arrangements previously described.

When a spray sealant is desired, any of the above described embodiments may further comprise an atomizing nozzle at the outlet port. Mixing occurs before atomization, assuring homogeneous sealant and the strongest gel while using a minimal amount of thrombin. However, interrupting sealant flow may lead to clogging the atomizing attachment and may thereby necessitate replacing the atomizing attachment.

Thus, either the present dispenser or the present mixing means may further comprise a means for atomizing effluent fluid in fluid connection to one end of said cylindrical fluid conduit in the means for applying the mixed fluids to the desired site of application.

A further aspect of the present invention concerns a method for applying two or more solutions of reactive components to a common site, comprising:

filling a first compartment of a multi-compartment applicator with a first reactant, filling a second compartment of said multi-compartment applicator with a second reactant, said second reactant being capable of instantaneously reacting with said first component, simultaneously dispensing the components of each of said compartments through a common location in a manifold into a mixing tip, from which the mixed components are applied to said site.

In the present method, the components may react to form a product selected from the group consisting of tissue sealant and epoxy glue. In a further embodiment, the compartments of said applicator have the same height but different cross-sectional areas, said components react to form tissue sealant and the compartment with larger cross section contains fibrin or fibrinogen solution. The applicator may have two compartments, and the compartment with smaller cross section may contain a thrombin solution.

Other features of the present invention will become apparent in the course of the following descriptions of the exemplary embodiments which are given for illustration of the invention, and are not intended to be limiting thereof.

EXPERIMENTS

Example 1
Plasma Gel Made with Mixing Needle

Figure 5:
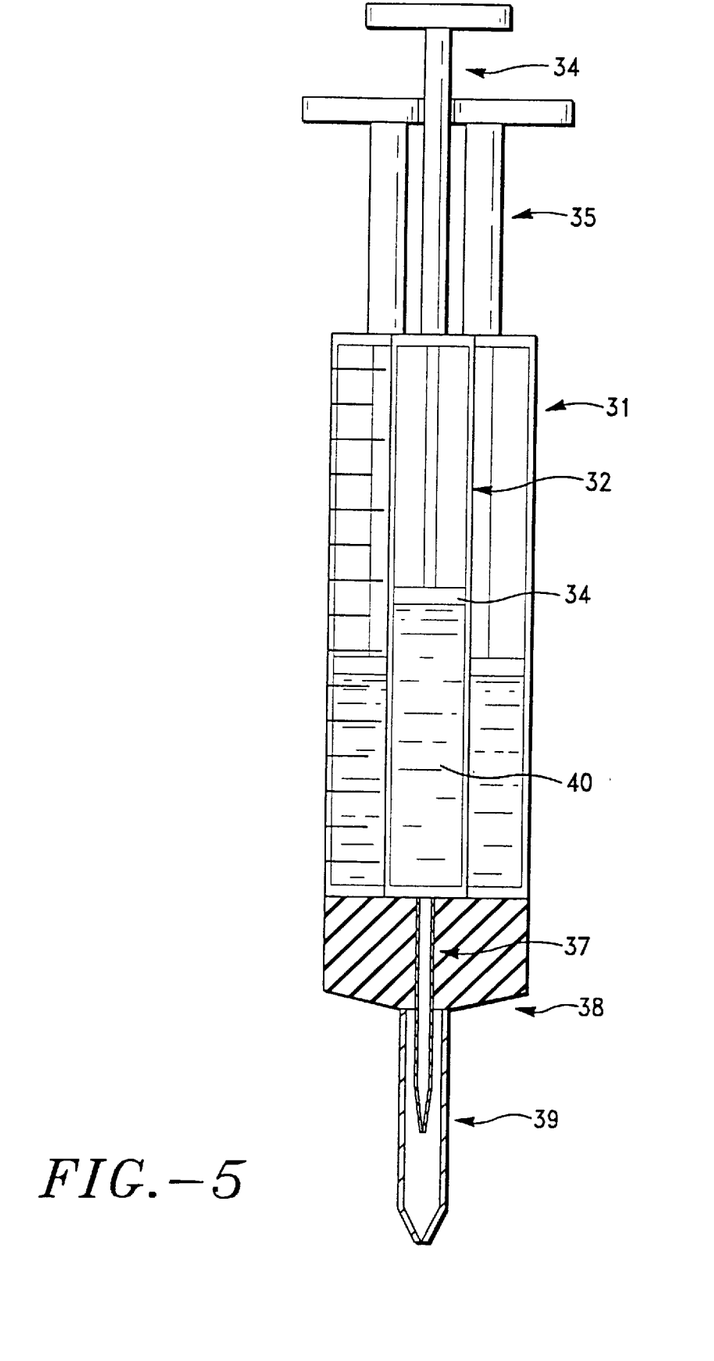
Figure 6:
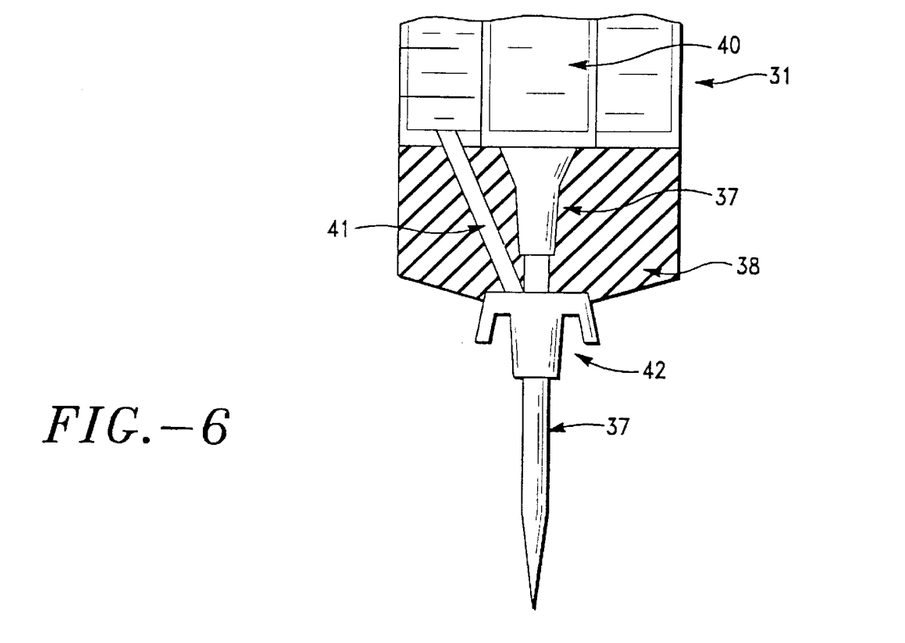
Figure 11:
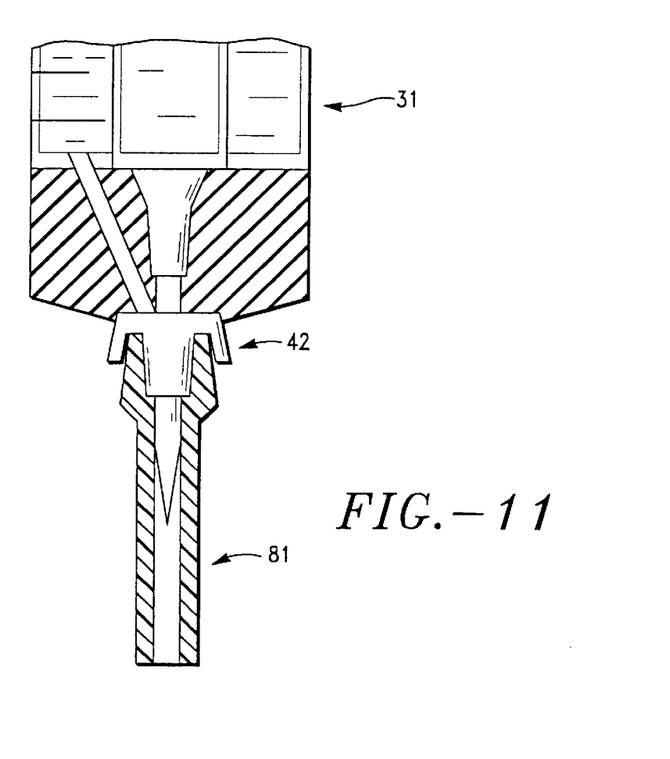
FIG. 11 shows a simple mixing needle tip 81 that does not clog, even if one intermittently applies sealant using the same applicator and component solutions.

One cubic centimeter of 300 millimolar calcium chloride solution containing 100 units of bovine thrombin was loaded into the inner compartment of a coaxially arranged two compartment dispenser constructed according to the design illustrated in FIG. 5. Ten cubic centimeters of porcine plasma separated by centrifugation (1500×g for 15 minutes) from whole blood collected in standard citrate anticoagulant solution was loaded into the outer compartment. The cross-sectional area of the outer compartment was 14.3 times greater than that of the inner compartment. The two solutions were expressed by pressing the button in the center of the plungers and simultaneously depressing both plungers. The thrombin solution was extruded through a standard 22 gauge hypodermic needle housed within a standard 18 gauge hypodermic needle (which served as conduit for the expressed plasma) the arrangement shown in FIGS. 5 and 11. The two solutions merged within the outer needle approximately 1 cm from the tip of the outer needle. The sealant was extruded in this manner directly into cylindrical mold cavities of 9.3 mm diameter and approximately 5 cm length. Coagulation of the extruded fluid occurred within approximately 5 seconds. Approximately 5 minutes were allowed to elapse between filling each of three molds. No noticeable increase in force was required to begin dispensing sealant into the molds after these interruptions of flow. After 20 minutes incubation at room temperature to allow factor XIII mediated crosslinking of the molded gels, the gels were removed from their molds, clamped at either end and assembled into a device for measuring tensile strength. Tensile strength was found to be 66±12 (mean±standard deviation) grams per square centimeter.

Example 2
Plasma Gel Film Made with Nebulizer

Figures 8, 9:
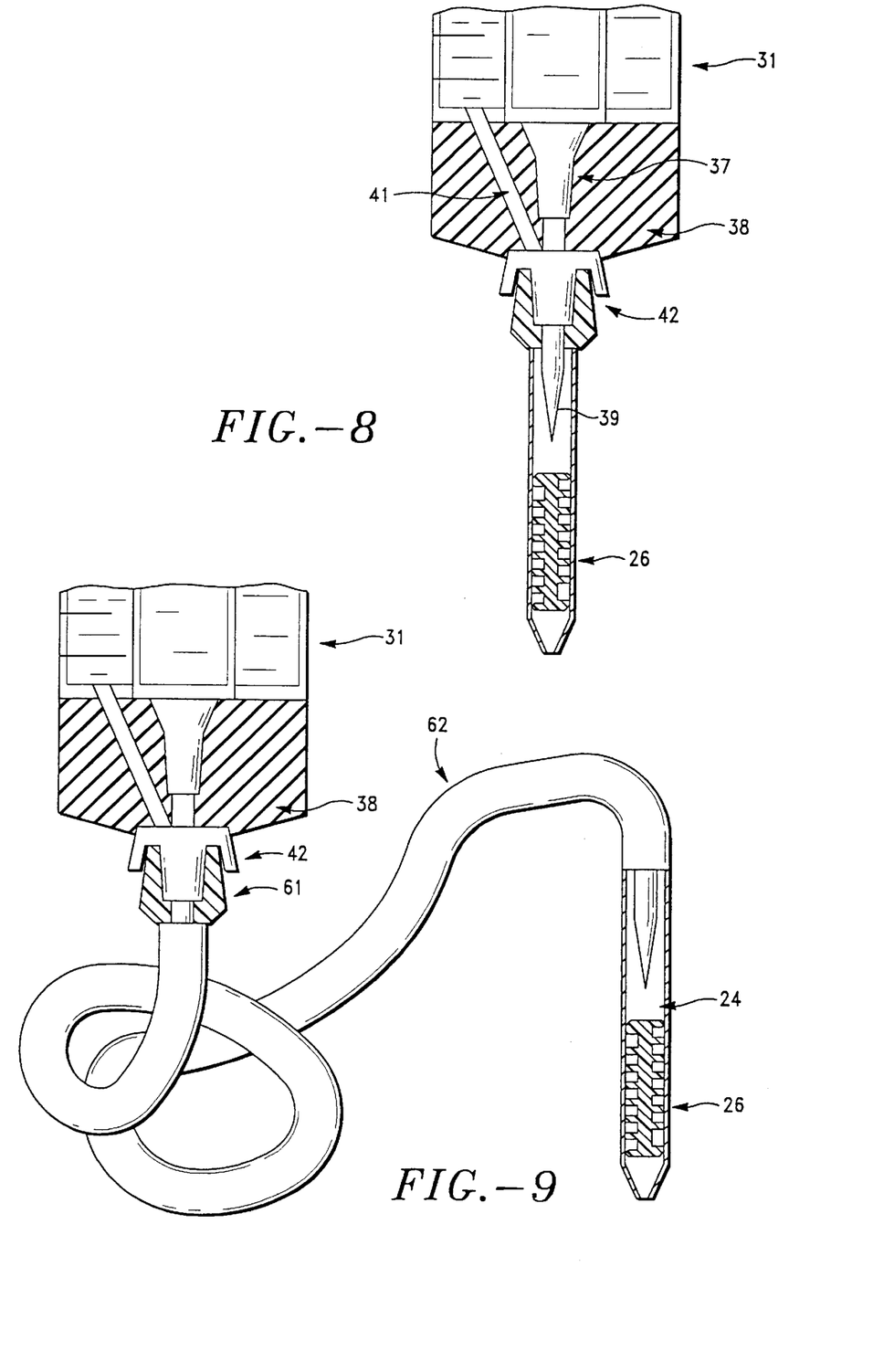
FIG. 8 shows a disposable static mixer tip 26 essentially identical to the one in FIG. 4.
FIG. 9 shows a flexible double lumen catheter 62 for application of tissue sealant at a distance from the syringe, (e.g., in a body cavity made accessible by laparotomy). The Luer lock 61 allows attachment of the double lumen catheter 62 to the syringe, permitting separation of the solutions as they travel through the catheter 62. The catheter ends with a disposable static mixer tip 26 essentially identical to the one in FIG. 4.
Figure 10:
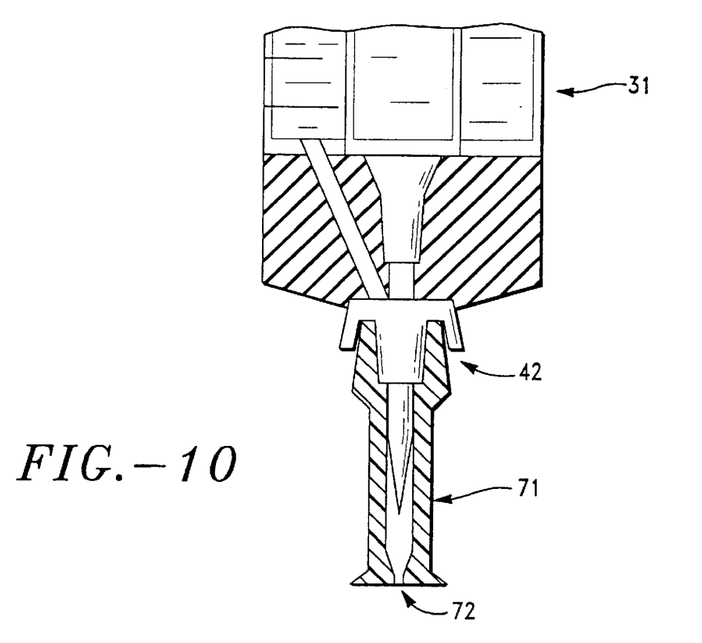

One cubic centimeter of 300 millimolar calcium chloride solution containing 100 units of bovine thrombin was loaded into the inner compartment of a coaxially arranged two-compartment dispenser constructed per the design represented by the illustration of FIGS. 5 and 10. Ten cubic centimeters of porcine plasma separated by centrifugation (1500×g for 15 minutes) from whole blood collected in standard citrate anticoagulant solution was loaded into the outer compartment. The cross-sectional area of the outer compartment was 14.3 times greater than that of the inner compartment. The two solutions were dispensed by pressing the button in the center of the plungers and simultaneously depressing both plungers. The thrombin-calcium solution was dispensed through the nebulizer tip shown in FIG. 8. The two solutions merged within the tip and emerged as a fine spray which was deposited on glass. Microscopic examination of the film showed a homogeneous thin layer of fibrin gel.

What is claimed as new and is desired to be secured by Letters Patent of the United States is:

1. A dispenser comprising:
   a plurality of separate parallel cylindrical compartments arranged concentrically, each of said cylindrical compartments having an outlet port at one end,
   a number of plungers equal to said plurality of cylindrical compartments, and
   a manifold having separate means for transporting fluid through the manifold from the outlet port of each cylindrical compartment to a common location on the surface of the manifold opposite said outlet ports.

2. The dispenser of claim 1, including means for actuating said plungers, wherein said means for actuating said plungers comprises a means for commonly actuating said plungers and a means for separately actuating said plungers.

3. The dispenser of claim 2, wherein said cylindrical compartments are coaxial, and said means for commonly actuating said plungers and said means for separately actuating said plungers comprise a coaxial inner plunger having a cap with a first diameter and a coaxial outer plunger having a coaxial cylindrical void into which said inner plunger is located, the diameter of said cap being greater than the diameter of said cylindrical void.

4. The dispenser of claim 2, wherein said means for commonly actuating said plungers comprises a rack and pinion mechanism.

5. The dispenser of claim 4, wherein each said plunger has a cap and said means for commonly actuating said plungers comprises means for mechanically connecting said pinion to the cap of each said plunger.

6. The dispenser of claim 1, wherein said cylindrical compartments comprise inner and outer concentric compartments, the inner concentric cylindrical compartment being fitted with an inner plunger, and the outer concentric compartment being fitted with a cylindrical plunger having a coaxial cylindrical void within which said inner plunger is located.

7. The dispenser of claim 1, wherein said plurality of cylinders is 2, said cylinders have equal heights, and the volume ratio of said cylinders is 10 or greater.

8. A dispenser comprising:

a plurality of separate parallel cylindrical compartments, arranged side-by-side, each of said cylindrical compartments having an outlet port at one end, a number of plungers equal to said plurality of cylindrical compartments, means for actuating said plungers, and a manifold having separate means for transporting fluid through the manifold from the outlet port of each cylindrical compartment to a common location on the surface of the manifold opposite said outlet ports, wherein said means for actuating said plungers comprises a rack and pinion mechanism for commonly actuating said plungers and means for separately actuating said plungers.

9. The dispenser of claim 8, wherein said plurality of cylinders is 2, said cylinders have equal heights, and the volume ratio of said cylinders is 10 or greater.

10. The dispenser of claim 8, wherein each said plunger has a cap and said means for commonly actuating said plungers comprises means for mechanically connecting said pinion to a cap of each said plunger.

* * * * *